United States Patent [19]

Hegner et al.

[11] Patent Number: 5,254,371
[45] Date of Patent: Oct. 19, 1993

[54] METHOD OF MANUFACTURING A CAPACITIVE HUMIDITY SENSOR

[75] Inventors: Frank Hegner, Lörrach; Traugott Kallfass, Grossbottwar, both of Fed. Rep. of Germany

[73] Assignee: Endress u. Hauser GmbH u. Co., Maulburg, Fed. Rep. of Germany

[21] Appl. No.: 751,169

[22] Filed: Aug. 28, 1991

[30] Foreign Application Priority Data

Sep. 12, 1990 [EP] European Pat. Off. ............ 9081689

[51] Int. Cl.⁵ .............................................. B05D 5/12
[52] U.S. Cl. .................................. 427/487; 427/525; 427/560; 427/601; 427/79; 427/126.3; 427/203; 427/204; 427/346; 427/387; 427/409; 427/419.2; 427/421; 361/178
[58] Field of Search ................. 361/178; 427/126.3, 427/203, 204, 409, 419.2, 487, 525, 560, 601, 79, 346, 387, 421

[56] References Cited

U.S. PATENT DOCUMENTS

| | | | |
|---|---|---|---|
| 4,438,480 | 3/1984 | Chambaz et al. | 361/278 |
| 4,482,882 | 11/1984 | Lüder et al. | 338/34 |
| 4,532,016 | 7/1985 | Chambaz et al. | 204/38.3 |
| 4,541,904 | 9/1985 | Lüder et al. | 204/192.35 |
| 4,603,455 | 8/1986 | Woest et al. | 427/79 |
| 4,761,710 | 8/1988 | Chen | 361/286 |

FOREIGN PATENT DOCUMENTS 0043775 1/1982 European Pat. Off. .
59-91355 5/1984 Japan .

Primary Examiner—Michael Lusigan
Assistant Examiner—Benjamin L. Utech
Attorney, Agent, or Firm—Barnes & Thornburg

[57] ABSTRACT

This method comprises the following steps, which are compatible with thin-film technology: forming a bottom electrode (2) on an insulating substrate (1), depositing a humidity-sensitive polymer layer (5) of uniform thickness on the bottom electrode (2) leaving contact areas (3a, 3b) uncovered, activating surface bonds of the polymer layer (5), applying a colloidal dispersion of $SiO_2$ or $Al_2O_3$ particles (6) of uniform grain size as a thin layer to the polymer layer (5) and subsequently drying it, depositing a cover electrode (7) on the particles (6) still evenly distributed on the polymer layer (5) after the drying of the dispersion, and removing the particles (6) together with the portions of the cover electrode (7) overlying them.

6 Claims, 2 Drawing Sheets

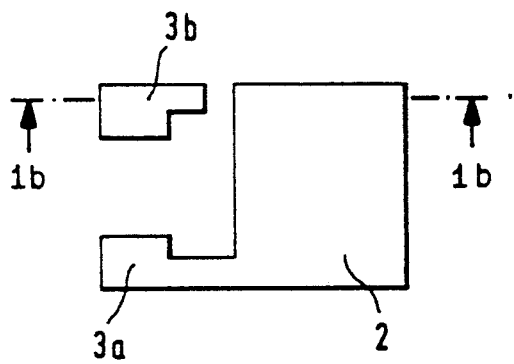
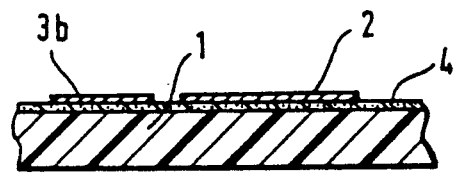
FIG. 1a    FIG. 1b
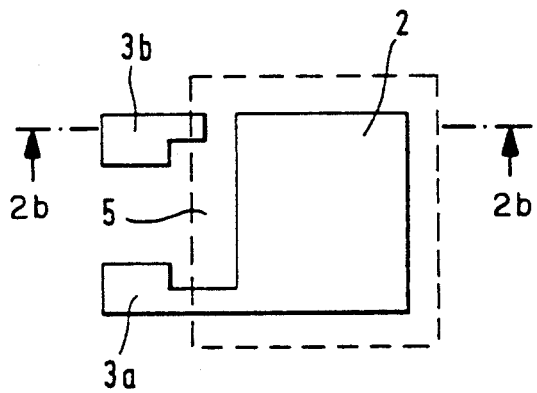
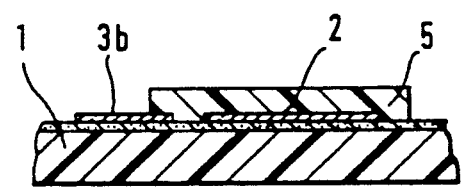
FIG. 2a    FIG. 2b
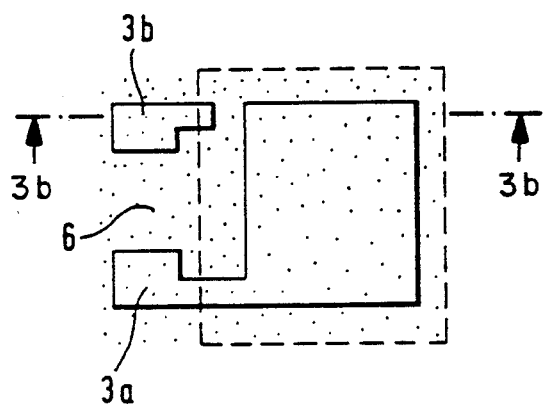
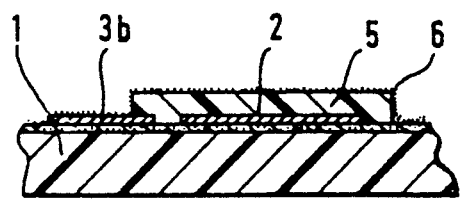
FIG. 3a    FIG. 3b

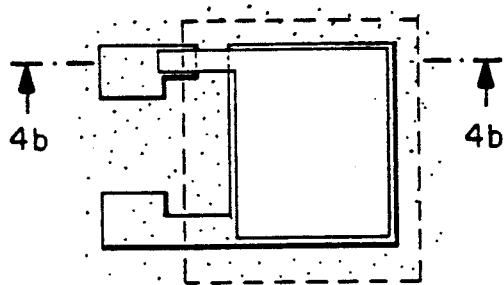
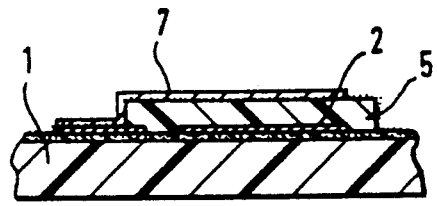
FIG.4a　　　　　　FIG.4b
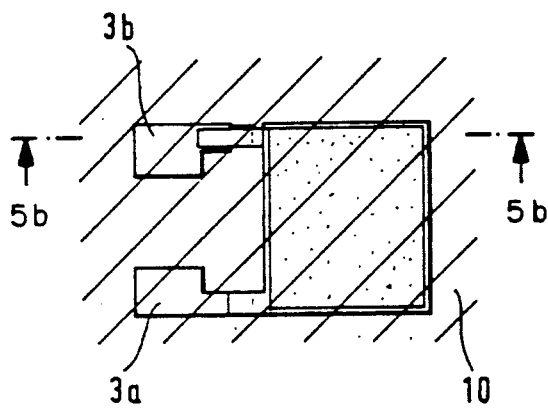
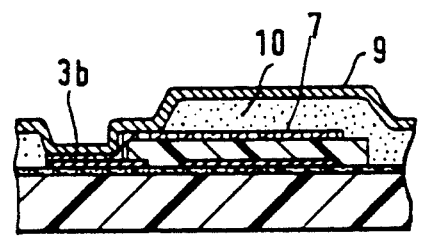
FIG.5a　　　　　　FIG.5b
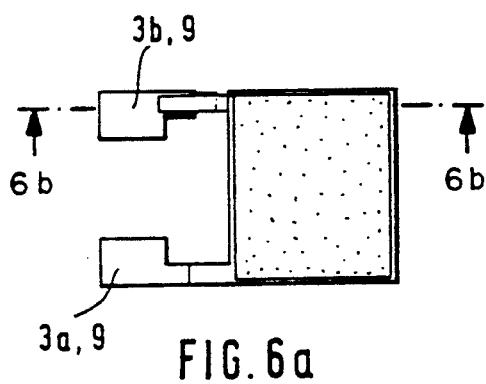
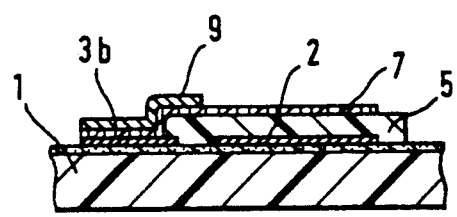
FIG.6a　　　　　　FIG.6b

METHOD OF MANUFACTURING A CAPACITIVE HUMIDITY SENSOR

BACKGROUND

The present invention consists in a method of manufacturing a capacitive humidity sensor comprising the following steps, which are compatible with thin-film technology: forming a bottom electrode on an insulating substrate, depositing a humidity-sensitive polymer layer of uniform thickness on the bottom electrode leaving contact areas uncovered, activating surface bonds of the polymer layer, applying a colloidal dispersion of $SiO_2$ or $Al_2O_3$ particles of uniform grain size as a thin Layer to the polymer layer and subsequently drying it, depositing a cover electrode on the particles still evenly distributed on the polymer layer after the drying of the dispersion, and removing the particles together with the portions of the cover electrode overlying them.

In such capacitive humidity sensors it must be ensured that the cover electrode is sufficiently permeable to water vapor, i.e., the absorption and desorption of the water molecules must not be impeded, so that a maximum speed of response is obtained. Furthermore, no water molecules must become attached to the edges of the openings in the cover electrode. The cover electrode must have a high mechanical, electric, and chemical long-term stability, which is important if humidity measurements are performed in the presence of aggressive substances, particularly if the temperature falls below the dew point, and/or at high temperatures.

Furthermore, the capacitive humidity sensor must be insensitive to contamination, which means that the electric field of the capacitor formed by it must not pass through the cover electrode. The cover electrode must exhibit no selective sensitivity to other gases (than water vapor); in particular, it must not act catalytically on such gases. Finally, the cover electrode must be sufficiently electrically conductive.

One could try to realize these properties by using a very thin Au layer (about 5 nm) as the cover electrode, which would be electrically unstable because of its island pattern, so that it would result in capacitance changes, and could practically not be mechanically loaded; or by using porous layers of Pt, Cr or Pd, which would also prove electrically unstable, would result in high and unstable transition resistances, and, in the case of Pt and Pd, would act catalytically (e.g., on $H_2$ and $NH_3$); or by providing cover electrodes having a comb structure, which, if their teeth were spaced more than 1 μm apart, would be sensitive to contamination because they could be penetrated by the electric field.

It is therefore the object of the invention to fulfil the above-explained requirements placed on capacitive humidity sensors better than hitherto by providing a novel method of manufacturing the same.

By the method according to the invention, the cover electrode is formed as a rugged and continuous metal layer, i.e., the aforementioned formation of islands is eliminated. In the cover electrode, evenly distributed microholes having a diameter of at least 0.1 μm to 1 μm, preferably 250 nm, are formed whose distribution density is so high that the mass of the cover electrode is reduced to a value at which, on the one hand, no islands are formed yet and, on the other hand, the required electric stability is reached, i.e., that despite the microholes, the cover electrode does not crack, for example. The microholes also largely avoid the above-mentioned penetration of the cover electrode by the electric field.

To form the microholes, the method according to the invention, while using conventional thin-film techniques, requires no mask, since a faithful reproduction of the image is unimportant. The even distribution of the microholes results automatically, so to speak, from the application of the $SiO_2$ or $Al_2O_3$ particles as a colloidal dispersion in the form of a thin, uniform layer, since the particles repel each other because of their electric charge. The particle density can be adjusted in a simple manner via the particle content of the colloid.

The polymer layer is preferably a layer of polyimide which is advantageously first applied as polyamide acid and then polymerized. In a preferred embodiment of the invention, the polyamide is activated by ion bombardment prior to the application of the colloid.

The application of the colloid to the polymer layer preferably takes place white the insulating substrate is rotating. Instead, the colloid may be sprayed on, or the insulating body is immersed in the colloid.

In another embodiment of the invention, an adhesive layer of a first metal is deposited on the particles, and the cover electrode of a second metal is deposited on this adhesive layer. The removal of the particles together with the portions of the cover electrode overlying them preferably takes place in a liquid by means of ultrasound.

BRIEF DESCRIPTION OF THE DRAWINGS

FIGS. 1a and 1b shows a substrate and bottom electrode (in plan and cross-section, respectively);

FIGS. 2a and 2b shows the substrate after deposition of the polymer layer (in plan and cross-section, respectively);

FIGS. 3a and 3b shows the substrate and polymer layer after deposition of a colloidal dispersion of particles thereon (in plan and cross-section, respectively);

FIGS. 4a and 4b shows the substrate, polymer layer and colloidal dispersion of particles after an upper electrode has been placed thereon and before the colloidal dispersion is activated to displace the particles through the upper electrode (in plan and cross-section, respectively);

FIGS. 5a and 5b shows the structure of FIGS. 4a and 5b after a lift-off photo-resist layer and bonding metal has been deposited (in plan and cross-section, respectively); and FIGS. 6a and 6b shows the structure of FIGS. 5a and 5b after the bonding material and lift-off layer has been removed by ultrasound (in plan and cross-section, respectively).

DETAILED DESCRIPTION OF THE DRAWINGS

FIG. 1 shows an insulating substrate 1, e.g., a glass or porcelain substrate. On this substrate, a bottom electrode 2, having a contact area 3a, with a thickness of 100 nm to 300 nm, preferably 200 nm, is deposited, e.g., by sputtering or vapor-depositing a suitable metal. Preferred metals for the bottom electrode 2 are Ta, Al and Cr. FIG. 1a also shows an additional contact area 3b, whose function will be explained below.

If, in a mass-production process, Ta is first deposited over an insulating piece of glass or porcelain to be separated in a last process step into individual capacitive humidity sensors, and then patterned by photolithographic techniques and wet-etched to form the bottom electrodes and contact areas, it is recommended to deposit a $Ta_2O_5$ etch-stop layer 4 over the entire surface prior to the etching step, so that etching of the insulating material is prevented. The etch-stop layer 4 may be deposited by sputtering or formed by oxidizing the Ta.

After formation of the bottom electrodes and contact areas, a humidity-sensitive polymer layer 5 is deposited which, as shown in FIG. 2, is patterned by photolithographic techniques such that the contact areas 3a, 3b are left uncovered, at least in part.

If, according to a preferred embodiment of the invention, the polymer layer 5 is a layer of polyamide, it is recommended to first apply polyamide acid as a liquid polyamide precursor by, e.g., spinning (while the insulating substrate 1 is rotating at high speed), to dry it prior to the patterning step, and then to polymerize it. The polyamide precursor may also be sprayed or rolled on. The preferred thickness of the polyimide layer is approximately 2.5 $\mu$m.

In the next step, a thin colloidal dispersion of $SiO_2$ or $Al_2O_3$ particles 6 of uniform grain size is applied to the polymer layer 5, preferably by spinning (see above) at a speed of, e.g., 5000 rpm to 7000 rpm for about 20 s.

A particularly even distribution of the $SiO_2$ or $Al_2O_3$ particles 6 is obtained if, according to a further embodiment of the invention, prior to the application of these particles 6 the surface of the polyamide is bombarded with ions, e.g., with Ar ions for about 3 min at a power density of 0.2 $W/cm^2$, whereby the surface bonds of the polyamide are activated.

For the colloid, a solvent must be chosen of which no residues remain after the drying which may react with water vapor or could affect the sensitivity of the humidity sensor.

On the particles 6 still evenly distributed over the polymer layer 5 after the drying of the colloid, a cover electrode 7 of metal is deposited in the process step of FIG. 4, preferably on an intermediate adhesive layer (not shown in the figures) of another metal. Particularly suitable metals for the cover electrode are Au, Au-Pd, Cr or Au-Cr. The preferred layer thickness is approximately 40 nm. Particularly suitable metals for the adhesive layer are Cr or Ti, and the preferred layer thickness is also 40 nm. The metals may be vapor-deposited or deposited by sputtering.

After the metal or metals of the cover electrode 7 have been patterned by photolithographic techniques, the particles 6 together with the portions of the cover electrode 7 overlying them are removed, which preferably takes place in a liquid by means of ultrasound.

To complete the humidity sensor, the contact areas 3a, 3b are provided with a suitable bonding metal 9, such as Au, as shown in FIG. 5. To this end, a lift-off photoresist layer of suitable thickness is first deposited on the finished cover electrode 7 and patterned in such a way as to leave only the bonding pads of the contact areas 3a, 3b uncovered. After this, the bonding metal 9 is deposited. Finally, the lift-off photoresist layer 10, together with the parts of the bonding metal 9 overlying it, is removed in a liquid by means of ultrasound. The contact area 3b serves to connect the cover electrode 7.

The finished humidity sensor is shown in FIG. 6.

We claim:

1. Method of manufacturing a capacitive humidity sensor comprising the following steps:
   forming a bottom electrode on an insulating substrate,
   depositing a humidity-sensitive polymer layer of uniform thickness on the bottom electrode leaving contact areas uncovered,
   activating surface bonds of the polymer layer by ion bombardment,
   applying a colloidal dispersion of $SiO_2$ or $Al_2O_3$ particles of uniform grain size as a layer of evenly distributed particles to the polymer layer and subsequently drying it,
   depositing a cover electrode on the particles still evenly distributed on the polymer layer after the drying of the dispersion, and
   removing the particles together with the portions of the cover electrode overlying them utilizing an ultrasound bath.

2. A method as claimed in claim 1 wherein the polymer layer is made of polyimide.

3. A method as claimed in claim 2 wherein polyimide acid is used as a polyimide precursor.

4. A method as claimed in claim 1 wherein the grain size of the particles is approximately 250 nm.

5. A method as claimed in claim 1 wherein the polymer layer and/or the dispersion of the particles on the polymer layer is sprayed or rolled on or is deposited while the insulating substrate is rotating.

6. A method as claimed in claim 1 wherein an adhesive layer of a first metal is deposited on the particles, and wherein the cover electrode of a second metal is deposited on said adhesive layer.

* * * * *